(12) United States Patent
Pope

(10) Patent No.: US 8,355,003 B2
(45) Date of Patent: Jan. 15, 2013

(54) CONTROLLER LIGHTING ACTIVATION BY PROXIMITY AND MOTION

(75) Inventor: Jeremiah M Pope, Kirkland, WA (US)

(73) Assignee: Microsoft Corporation, Redmond, WA (US)

( * ) Notice: Subject to any disclaimer, the term of this patent is extended or adjusted under 35 U.S.C. 154(b) by 498 days.

(21) Appl. No.: 12/139,227

(22) Filed: Jun. 13, 2008

(65) Prior Publication Data

US 2009/0312101 A1    Dec. 17, 2009

(51) Int. Cl.
*G06F 3/02* (2006.01)

(52) U.S. Cl. ........... 345/170; 345/156; 345/168; 463/37

(58) Field of Classification Search .......... 345/156–184; 178/18.01, 18.02, 18.03; 463/36, 37
See application file for complete search history.

(56) References Cited

U.S. PATENT DOCUMENTS

| | | | |
|---|---|---|---|
| 5,854,621 A | 12/1998 | Junod et al. | |
| 6,238,289 B1 | 5/2001 | Sobota et al. | |
| 6,402,616 B1 * | 6/2002 | Ogata et al. | 463/37 |
| 6,661,410 B2 | 12/2003 | Casebolt et al. | |
| 6,703,599 B1 | 3/2004 | Casebolt et al. | |
| 6,773,128 B2 | 8/2004 | Katrinecz, Jr. et al. | |
| 6,859,196 B2 | 2/2005 | Kehlstadt | |
| 7,010,710 B2 | 3/2006 | Piazza | |
| 7,236,154 B1 | 6/2007 | Kerr et al. | |
| 2001/0024973 A1 | 9/2001 | Meredith | |
| 2002/0095222 A1 | 7/2002 | Lignoul | |
| 2002/0103024 A1 * | 8/2002 | Jeffway et al. | 463/36 |
| 2003/0006965 A1 * | 1/2003 | Bohn | 345/163 |
| 2003/0162558 A1 * | 8/2003 | Takase et al. | 455/550 |
| 2004/0192413 A1 | 9/2004 | Frank | |
| 2005/0114714 A1 | 5/2005 | Albulet | |
| 2005/0177929 A1 | 8/2005 | Greenwald et al. | |
| 2005/0201291 A1 | 9/2005 | Gluck | |
| 2006/0035590 A1 | 2/2006 | Morris et al. | |
| 2006/0081771 A1 | 4/2006 | Wardimon | |
| 2006/0111187 A1 | 5/2006 | Miyazaki | |
| 2007/0046634 A1 | 3/2007 | Rice, Jr. | |
| 2007/0097065 A1 * | 5/2007 | Kreek et al. | 345/102 |
| 2007/0296701 A1 | 12/2007 | Pope et al. | |

(Continued)

FOREIGN PATENT DOCUMENTS

| | | |
|---|---|---|
| KR | 10-2005-0065197 A | 6/2005 |
| WO | WO 02/10886 A2 | 2/2002 |
| WO | WO 2005/057988 A1 | 6/2005 |
| WO | WO 2007/081402 A1 | 7/2007 |

OTHER PUBLICATIONS

Decision on Appeal, *Ex parte Yen-Kuang Chen*, Appeal 2009-004091, Apr. 27, 2010.*

(Continued)

*Primary Examiner* — Amare Mengistu
*Assistant Examiner* — Dmitriy Bolotin
(74) *Attorney, Agent, or Firm* — Woodcock Washburn LLP

(57) ABSTRACT

Mechanisms for controlling lighting activation by taking into account proximity and motion data are disclosed. Controllers can have cosmetic and/or functional lighting that can be controlled by proximity detectors and/or motion detectors, and such lighting can vary in color, intensity, and/or pattern. Proximity detectors can use capacitance, lighting, and/or sound data to determine the proximity of objects to the controllers, and motion detectors can use accelerometers and/or gyroscopes to determine the motion of such controllers. Additionally, controllers can start radio frequency communications with gaming consoles based on proximity and/or motion data. One benefit of such proximity and/or motion light control is battery conservation.

19 Claims, 10 Drawing Sheets

U.S. PATENT DOCUMENTS

| | | | |
|---|---|---|---|
| 2008/0018604 A1* | 1/2008 | Paun et al. | 345/168 |
| 2008/0077422 A1 | 3/2008 | Dooley et al. | |
| 2008/0084385 A1 | 4/2008 | Ranta et al. | |
| 2008/0096657 A1* | 4/2008 | Benoist | 463/36 |
| 2008/0218493 A1* | 9/2008 | Patten et al. | 345/173 |
| 2009/0139778 A1* | 6/2009 | Butler et al. | 178/18.03 |
| 2009/0161579 A1* | 6/2009 | Saaranen et al. | 370/254 |
| 2009/0225038 A1* | 9/2009 | Bolsinga et al. | 345/173 |
| 2009/0227232 A1* | 9/2009 | Matas et al. | 455/411 |

OTHER PUBLICATIONS

PCT Application No. PCT/US2009/045924: International Search Report and Written Opinion of the International Searching Authority, Jan. 13, 2010.

Bokme, L. et al., "Capacitive Front Panel Display Demonstration", Cypress Semiconductor Corporation, Revision E of Application Note, Oct. 20, 2005, 7 pages.

Hammer et al., "How to set CSR Parameters", Internal Correspondence at Cypress Semiconductor Corporation, Nov. 28, 2005, 14 pages.

Viredaz, M.A. et al., "Energy Management on Handheld Devices", *ACM*, Oct. 2003, http://www.hpl.hp.com/techreports/2003/HPL-2003-184.pdf, 11 pages.

Udani, S. et al., "The Power Broker: Intelligent Power Management for Mobile Computers", 1996, http://citeseer.ist.psu.edu/cache/papers/cs/7932/http:zSzzSzwww.cis.upenn.eduzSz~udanizSzpaperszSzbroker1.pdf/udani96power.pdf, 13 pages.

* cited by examiner

CONTROLLER LIGHTING ACTIVATION BY PROXIMITY AND MOTION

CROSS-REFERENCE TO RELATED APPLICATION

The present application may be related in subject matter to the following application: U.S. Publication No. 2007/0296701, U.S. Ser. No. 11/474,119, entitled "Input Device Having a Presence Sensor."

COPYRIGHT NOTICE AND PERMISSION

A portion of the disclosure of this document may contain material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice shall apply to this document: Copyright © 2008 Microsoft Corp.

FIELD OF TECHNOLOGY

The presently disclosed subject matter relates to the field of computing, and more particularly, to fields such as gaming, although this is merely an exemplary and non-limiting field.

BACKGROUND

For some gaming accessories lighting can be a important part of the experience of using the devices. Both cosmetic and functional lighting can be an integral part of any gaming device. The use of lighting can be enhanced if various systems and methods are used to control such lighting based on user context—for example, based on whether users are holding gaming devices or not, based on how close such devices are to users, and based on the motion of such devices when handled by users. To this end, it would be advantageous to provide various mechanisms for controlling lighting activation by taking into account user proximity and motion.

SUMMARY

Various mechanisms are provided herein for controlling lighting activation by taking into account proximity and motion data. Controllers can have cosmetic and/or functional lighting that can be controlled by proximity detectors and/or motion detectors. Proximity detectors can use a predetermined standard, such as capacitance, light, including visible light or infrared light, or ultrasonic sound, in order to determine the proximity of objects (whether users of gaming systems or any individuals) to the controllers. Motion detectors can use accelerometers and/or gyroscopes to determine the motion of such controllers. In some aspects of the presently disclosed subject matter, controllers can start radio frequency communications with gaming consoles based on proximity and/or motion data. In other aspects, such proximity and/or motion controlled lighting can vary in color, intensity, and/or pattern.

It should be noted that this Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The foregoing Summary, as well as the following Detailed Description, is better understood when read in conjunction with the appended drawings. In order to illustrate the present disclosure, various aspects of the disclosure are shown. However, the disclosure is not limited to the specific aspects shown. The following figures are included.

DETAILED DESCRIPTION

Overview

Various mechanisms are presented herein, including systems, methods, computer readable media, and so forth, for the controlling of lighting on various controller devices (although hardware device are not the only type of entities considered herein, since software modules are also contemplated). By way of example, proximity detectors and motion detectors can be used to ensure that the lighting levels on controllers are appropriate for a given situation. If users are close to, approaching, or actually touching a controller, the lighting level on the controller can change automatically (e.g. from an off-state or dimmed-state to an on-state). Similarly, if users are moving a controller in a certain direction (or at all) the lighting level can change. Various ways to control lighting are presented herein, however, other equivalent manners to controlling lighting are also contemplated herein, as those of skill in the art would readily appreciate.

Aspects of Lighting Activation by Proximity and Motion

Figure 1:
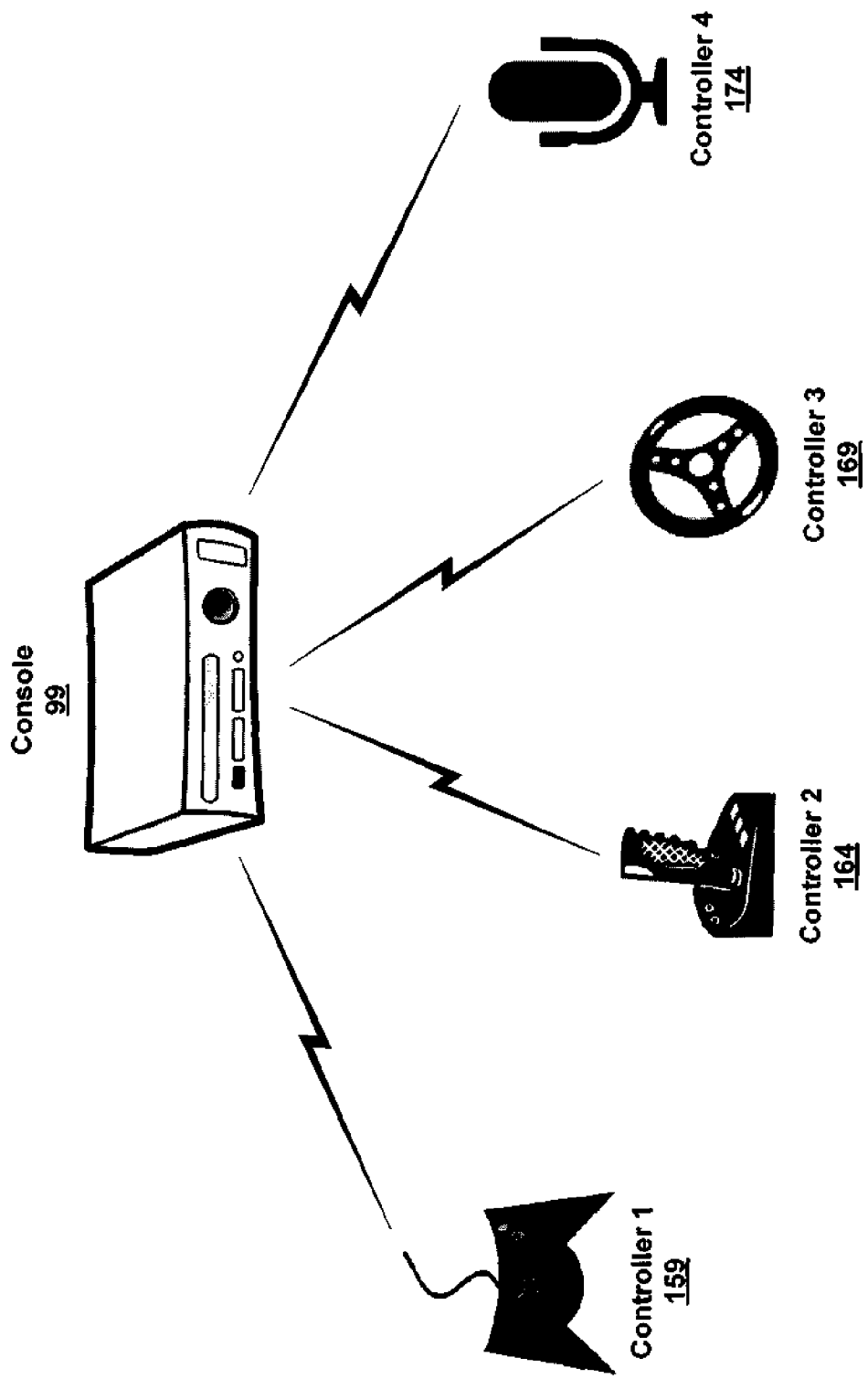
FIG. 1 illustrates that in the prior art various controller devices communicated with gaming consoles.

FIG. 1 illustrates a prior system where multiple controllers communicate with a console. Specifically, console 99, communicates with a plurality of controllers: a traditional gaming controller 1 159, with various buttons; a joystick controller 2 164; a steering wheel controller 3 169; and, a microphone controller 174 (where, for example, users can sing into the microphone and interact with a game running on the console 99).

In these controllers, lighting levels can be controlled by the console via some radio frequency communications. Thus, the traditional controller 1 159 can display on and off lighting and provide other feedback mechanisms, such as vibrations. However, none of the controllers 159, 164, 169, 174 in FIG. 1 have lighting that is controlled based on input for any one (or a combination of) proximity detectors and/or motion detectors.

Figure 2:
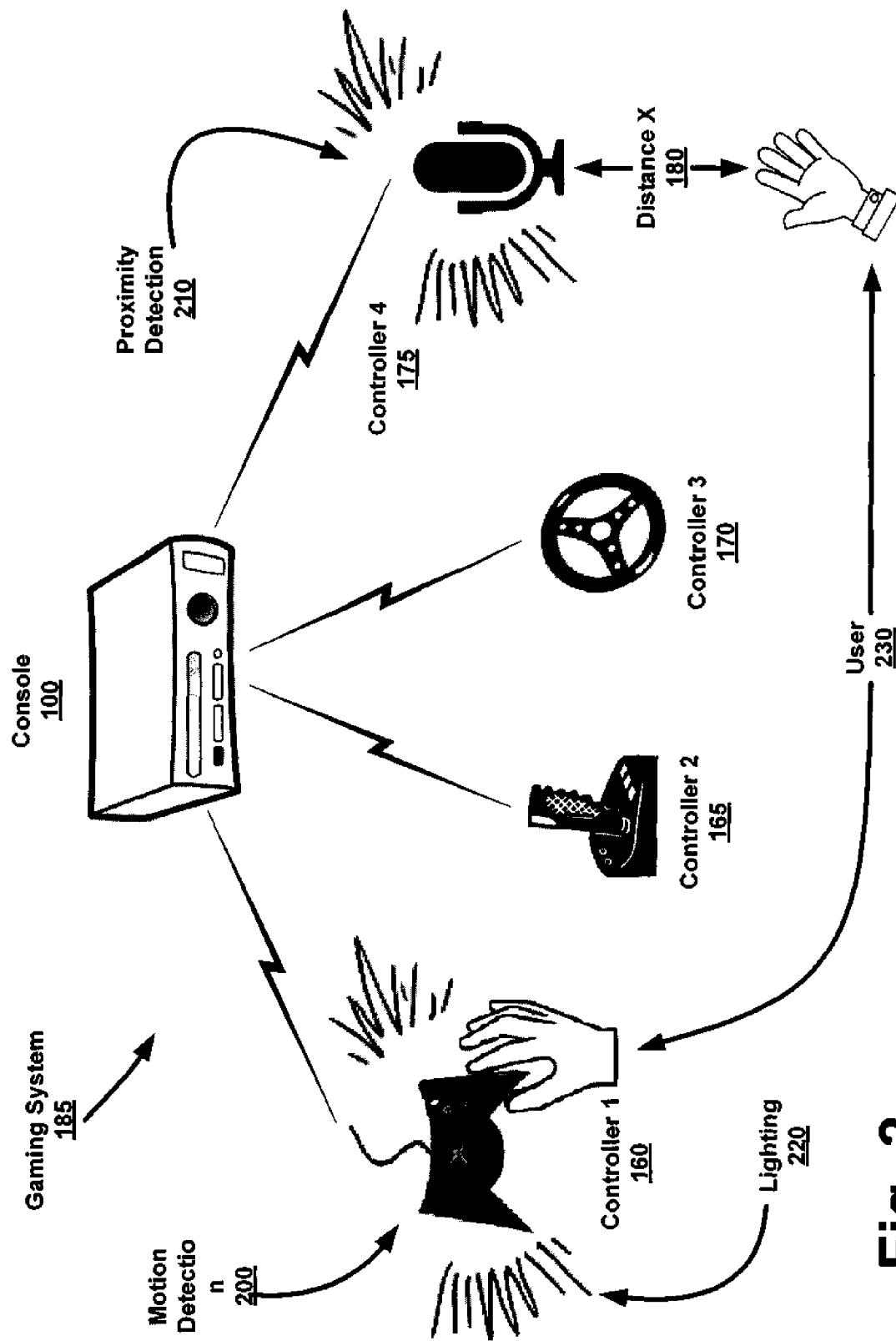
FIG. 2 illustrates that in contrast to FIG. 1, in one aspect of the present disclosure, the lighting on controller devices can be controlled by motion and/or proximity detection.

In contrast, FIG. 2 illustrates that in one aspect of the present disclosure, the lighting on controllers can be controlled by motion and/or proximity detection. For example, a traditional gaming controller 1 160 can have a plurality of lights that light up when motion 200 is sensed. In the alternative (or even additionally), controllers can also light up when they sense the proximity of objects (such as individuals or users of the console 100, but not limited thereto). Thus, a microphone controller 4 device 175 can light up when it senses that a user 230 of the gaming system 185 is nearby (such as being a predetermined distance X 180 away).

In FIG. 2, any of the shown controllers 160, 165, 170, 175 can employ any one or a combination of motion detection 200 and/or proximity detection 210. Various heuristics can be used regarding how the output of such detection 200, 210 will be used. For example, in the case of controller 4 175 (e.g. a microphone), when a user either approaches (or recedes from), is near to, or touches controller 4 175, it can light up, per proximity detection 210. Then, as the user is singing into controller 4 175, motion detection can additionally control any lighting, so that when controller 4 175 is held still one level and one type of lighting can be displayed (e.g. green light), but when the users starts to wildly move controller 4 175 around, various other colors (e.g. strobe-like lighting with various colors) can start to light up controller 4 175. This is, of course, a merely exemplary heuristic, the point being that motion detection and/or proximity detection 210 can be used in any manner, alone or in combination, to control any lighting on the shown controllers 160, 165, 170, 175.

Figure 3:
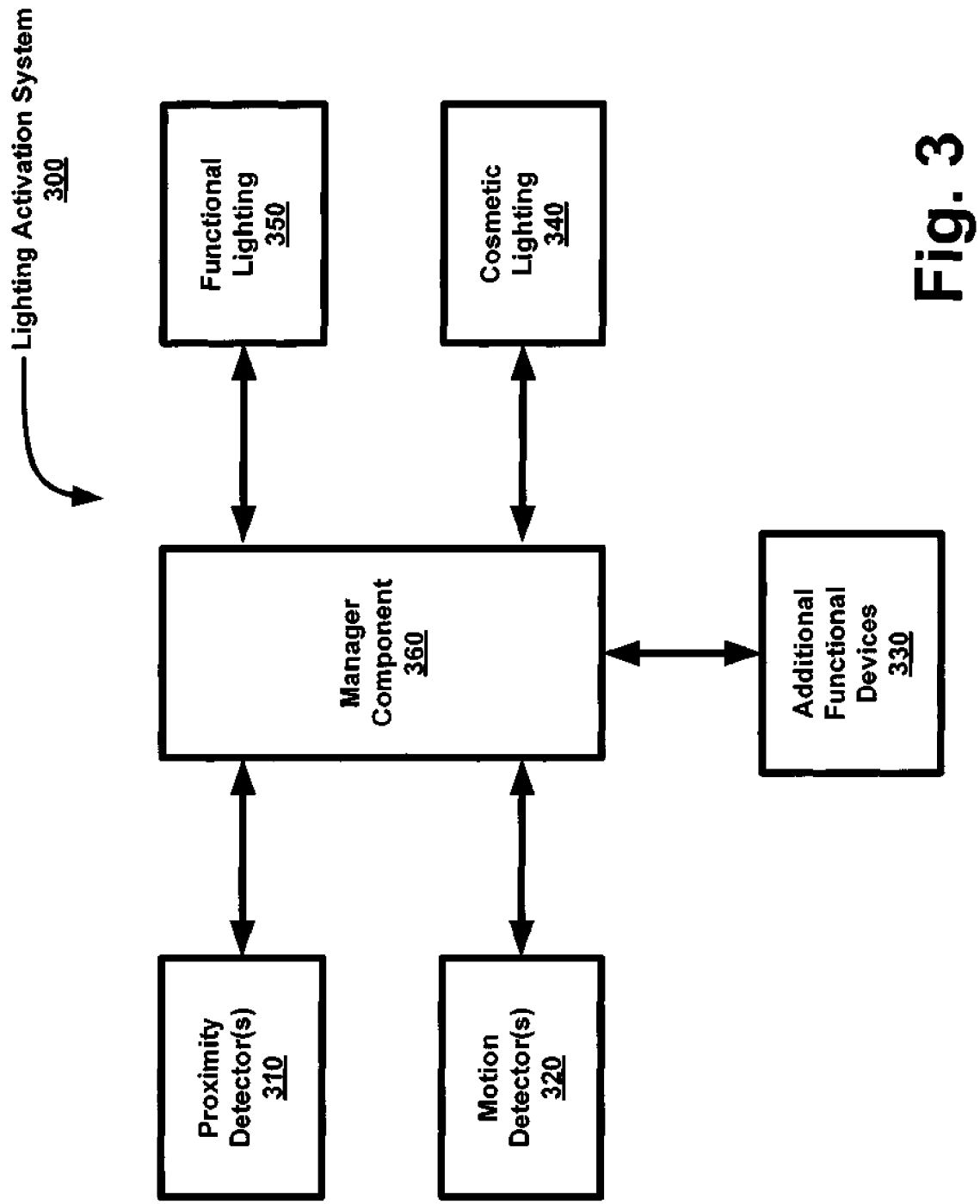
FIG. 3 illustrates an exemplary and non-limiting system that could implement the shown set-up in FIG. 2.
Figure 4:
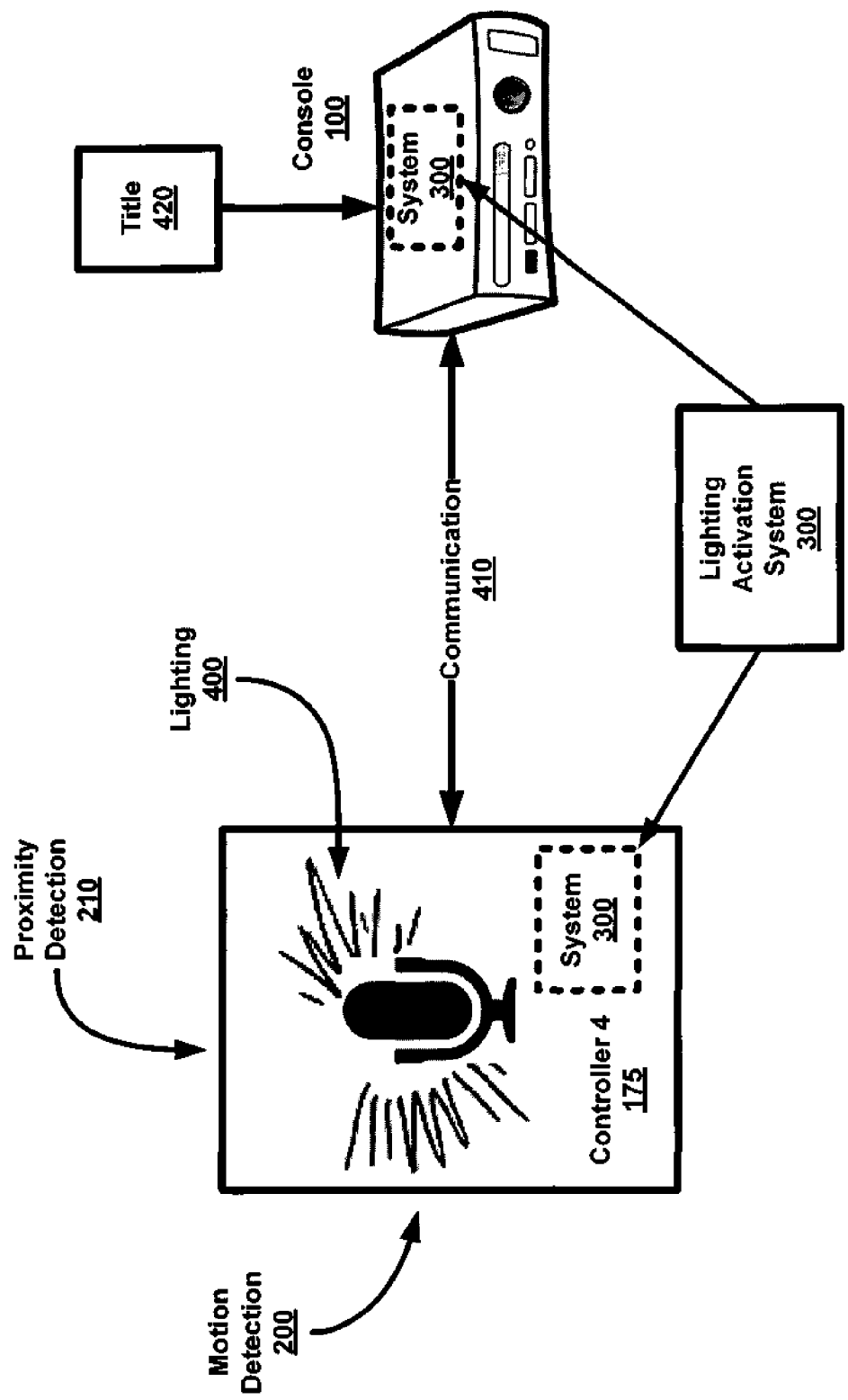
FIG. 4 illustrates that the light activation system could be wholly located in a controller device, or wholly located in a console, or partly located in each the controller device or the console.

Next, FIG. 3 illustrates an exemplary system that could implement the shown set-up in FIG. 2. A light activation system 300 could comprise a proximity detector 310 configured to determine proximity based on a predetermined standard, such as capacitance, light, including visible light or infrared light, ultrasonic sound (or radar). Proximity could be detected substantially around and on (e.g. touching) a controller device. The system 300 could also comprise a motion detector 320 configured to detect the motion of a controller device, where the motion could be determined from the output of an accelerometer device and/or a gyroscope device installed in the controller (this could be in a single axis, front-to-back, or multiple axes, X/Y/Z & Roll/Pitch/Yaw, devices). The system 300 could have functional lighting 350 that could be used as part of a game (e.g. singing into a microphone in response to cues given by a game) or mere cosmetic lighting 340 that may not serve any functional purpose but that may be aesthetically pleasing. Additional functional devices 330 are also contemplated herein, such as acoustic, vibrational, visual, musical, and other devices that could work in concert with the functional lighting 350 and cosmetic lighting 340.

The lighting activation system 300 could also include a manager component 360 that can govern or control the proximity detector 310, the motion detector 320, the cosmetic 340 and functional 350 lighting, as well as any additional functional devices 330. The manager component 360 could be configured to receive input data from the proximity detector 310 and input data from the motion detector 320. And, it could be further configured to determine at least one of whether an object, such as an individual, is holding a controller device, is near a controller device, and/or is approaching a controller device based on the input data from the proximity detector 310. Additionally, the manager component 360 could be configured to determine whether and how a controller device is being moved by an individual based on the input data from said motion detector. Together, the proximity and motion data could give a controller device enough information to determine when an individual wants to use the controller device (and hence preemptively light itself up). Thus, the manager component 360 could be further configured to control the lighting level of at least one light of a plurality of lights on a controller device based on the input data from the proximity detector and the motion detector. As mentioned, other devices 330 could provide additional data for better accuracy of turning lights at the correct time.

There are various aspects to the light activation system 300. By way of example, the lighting level of any controller can be set to at least one of a maximum setting, an off setting, and a range of dimmed settings in between the maximum setting and the off setting. In general, controller lighting can encompass a spectrum of different light intensities, colors, and/or patterns. For example, with respect to light intensities, they can be controlled via pulse width modulation.

In another aspect of the present disclosure, whether an individual is holding a controller device can be based on a first capacitance level, and whether an individual is near a controller device can be based on a second capacitance level. Thus, a first threshold level for capacitance can be designated as the equivalent of holding a controller device, say X picofarads. Similarly, a second threshold level for capacitance can be designated as the equivalent of for being near a controller device, say Y picofarads, which may translate to three inches in distance between a controller device and an individual. Finally, whether an individual is approaching a controller device can be based on a changing capacitance level. Thus, if the capacitance level is changing from a first value, say A, to a second value, say, B, then it can be inferred that an individual is approaching a controller. (It should be noted, however, that other predetermined standards other than capacitance could be used—light, sound, etc.—as mentioned above). In this scenario, lights on the controller device can be turned on (whether instantly or gradually, depending on the implementation). For instance, the lights on the controller device can get brighter and brighter as an individual is approaching closer and closer to the controller.

In still another aspect of the presently disclosed subject matter, whether a controller device is being moved by an individual can be based on acceleration data and/or gyroscope data levels. For instance, certain threshold levels can be set that can correspond to movement of a controller. Thus, a determination can be made right away whether a controller has been moved at all. Moreover, how a controller device is being moved in three dimensional space by an individual can be based on a changing acceleration data and/or gyroscope data. For instance, various changes in acceleration can help to determine how far a controller device has moved, and various changes in gyroscope data can help to determine the orientation of a controller device. Together, the accelerometer and gyroscope data can track a controller's movement in space, and this data can then be used as a basis for controlling lighting on the controller device (not to mention that such data can also affect the content of a game playing on a remote console with which the controller device is communicating).

In one aspect of the presently disclosed subject matter, a controller device can be configured to control at least one light of a plurality of lights based on motion of an individual who is holding the controller. In another aspect of the presently disclosed subject matter, a controller device can be configured to control at least one light of a plurality of lights based on movement of content in a game. Thus, character movement or song content in a game can be reflected in the lighting on the controller device. Thus, in general terms, not only can objects in the real world have impact on the lighting of a controller device (e.g. game users moving about the controller), but additionally objects in the virtual world (viz. game content) can have impact on the lighting of the controller device. One real world example might be a karaoke game that can dictate when users should start singing into a microphone by lighting up the microphone. Users can move the microphone around and the lighting might change in response to the movement (in color, intensity, and pattern). Finally, when users put down the microphone, the lighting can be dimmed or turned off entirely—depending on the implementation.

The aforementioned manager component 360 that is part of the overall lighting activation system 300 can reside in a variety of places. While the proximity detector 310 and the motion detector 320 could reside inside a controller device, the actual manager 360 could reside either wholly inside the controller, wholly outside the controller (such as in a gaming console), or partly inside the controller and party inside the console, depending on the implementation.

In another aspect of the presently disclosed subject matter, the controller device could start radio frequency communications between a gaming console and the controller device based on data from a proximity detector. Thus, if the controller device detected that a user was approaching the controller device it could start radio frequency communications with the console, resulting in the appearance to the user that the connection was either instantaneous or already pre-existing. This setup would be beneficial in saving battery life, since in actuality the controller device would not have to maintain communications with the console, but only start to initiate them when users were approaching the controller (i.e. intending to use the controller to start playing games on the console). Thus, in one aspect of the presently disclosed subject matter, the communications could be started before an individual touches a controller.

As for the controller device itself, it could be any one or a combination of: (a) a traditional gaming controller 160, (b) a joystick 165, (c) a steering wheel 170, (d) a microphone 175, and (e) a music device (not shown in FIG. 2), or (f) any accessory device capable of interfacing with a gaming console, such as a physical gesture device (e.g. a balance/exercise board or any device that conveys physical gesture data).

Figure 5:
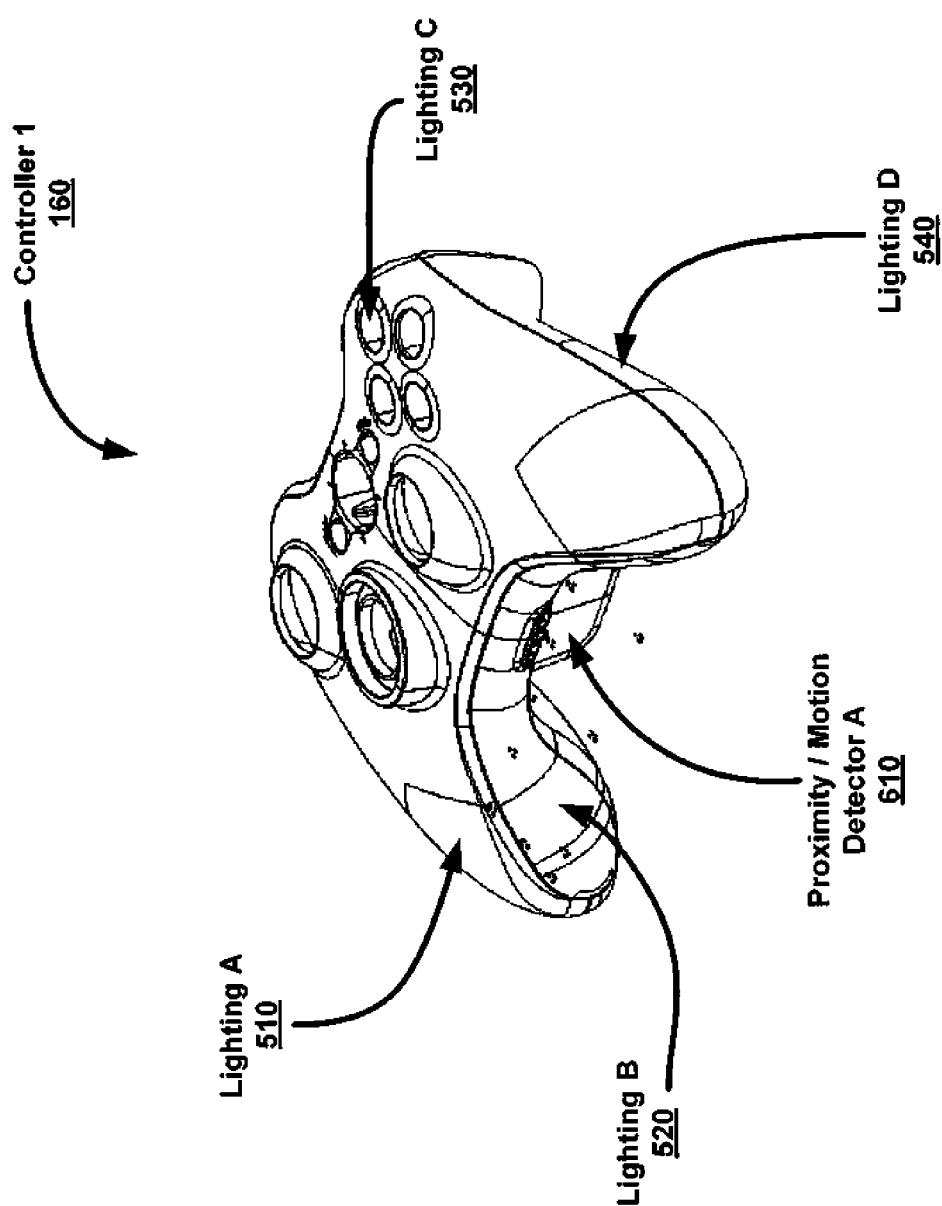
FIG. 5 illustrates a first aspect of one exemplary type of peripheral device that could implement lighting features based on proximity and motion.

In another aspect of the presently disclosed subject matter, FIG. 5 illustrates a first aspect of one exemplary type of peripheral device that could implement lighting features based on proximity and motion. FIG. 5 shows a traditional controller device shown in FIG. 2—controller 1 160. However, it should be understood that any type of controller or accessory to a console can employ the lighting activation mechanisms described above.

Per FIG. 5, controller 1 160 can have lighting A 510 on the top of the controller 1 160, on the inside side (as shown by lighting B 520), on the outside side (as shown by lighting D 540), on certain (or all) buttons (as shown by lighting C 530, and so on. The lighting can be located anywhere on controller 1 160, whether such lighting is used for cosmetic/aesthetic purposes or for functional purposes. Similarly, the proximity and motion detectors 610 can be located anywhere on or on the inside of controller 1 160. For example, the detectors 610 can be located near the center of mass of the controller 160 (yet in other aspects, they can be located elsewhere—depending on the implementation).

Figure 6:
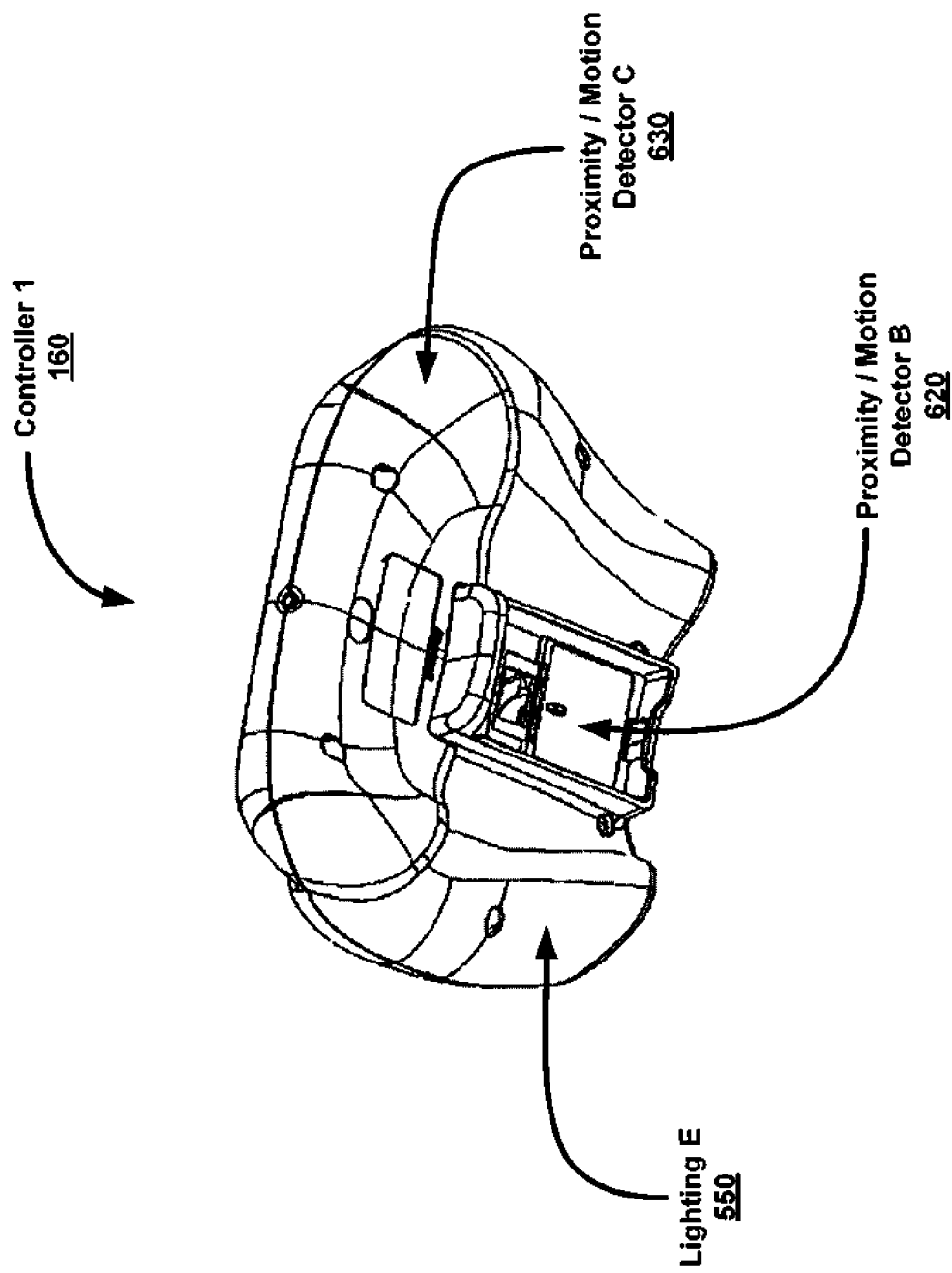
FIG. 6 illustrates a second aspect of one exemplary type of a peripheral device that could implement lighting features based on proximity and motion.
Figure 7:
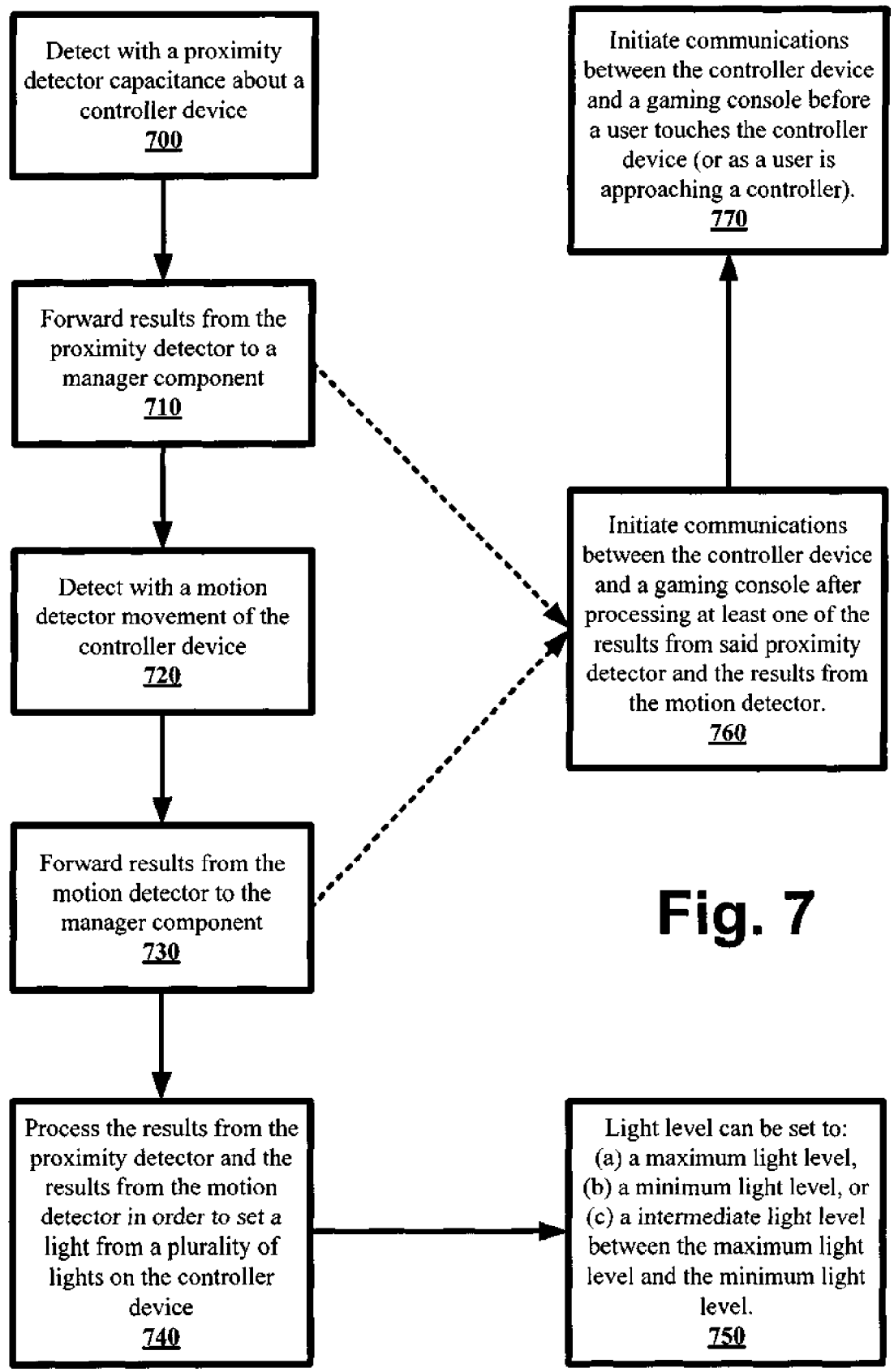
FIG. 7 illustrates an exemplary method for implementing the presently disclosed subject matter.

Next, FIG. 6 further illustrates a second aspect of the one exemplary type of peripheral device shown in FIG. 5. In FIG. 6, controller 1 160 could have lighting E 550 located on the underside of controller 1 160, and it could have proximity and motion detectors 620, 630 located on sides or center of controller 1 160. In one aspect of the presently disclosed subject matter, the proximity and/or motion detector B 620 could be removable from (or added to) controller 1 160 much in a similar manner to which batteries are added or removed from controllers. In any event, it should be noted that the lighting and proximity and motion devices could be located anywhere on and anywhere in controller device 1 160.

In another aspect of the presently disclosed subject matter, an exemplary method could be implemented for controlling lighting activation on controller devices configured to communicate with remote gaming consoles. However, it should be understood that similar systems, computer readable media, and other mechanisms could be used to carry out this aspect of the presently disclosed subject matter. At block 700, a proximity detector could be used to detect capacitance about a controller device. This detection could be done on the surface of the controller or extend to some close distance from the controller (e.g. several inches or centimeters). Next, at block 710, the results of the detection could be forwarded to a manager component that could process the results and use this data as a basis for controlling lighting activation on the controller.

Similarly, at block 720, a motion detector could be used to detect the movement of the controller device. As was mentioned above, various devices could be used by the motion detector to accomplish this goal, including but not limited to an accelerometer and/or a gyroscope. At block 730, the results could be forwarded from the motion detector to a manager component. Again, the manager component could use the forwarded data to control lighting activation on the controller device. It should be noted that the manager component could use the proximity data alone or the motion data alone to activate any lighting. In the alternative, the manager component could use a combination of the proximity data and the motion data to control lighting. In still other aspects of the disclosed subject matter, this combination along with data from other devices could be used, depending on the implementation and the level of accuracy desired.

Thus, block 740 shows that the above mentioned results could be processed by the manager component to display cosmetic and/or functional lighting according to some desired heuristic. Such heuristics can vary depending on the content of a game being played on a console. For instance, steering wheel lights in a racing game can subscribe to different heuristics than microphone lights in a karaoke game. Heuristics can be based on how fast a controller device is moved, how far away it is from a users, a combination of movement and location, and other motion-based parameters that could also be the basis for heuristics: direction of travel, orientation with respect to gravity, distance from a reference point, timing of motion (in rhythm with music, for example), and so on.

At block 750, the lighting level could be set to a level that is at least one of (a) a maximum light level, (b) a minimum light level, and (c) a intermediate light level between the maximum light level and the minimum light level. In one aspect of the presently disclosed subject matter, upon detection of motion and/or proximity, communications could be initiated between the controller device and a gaming console after processing at least one of the results from the proximity detector and the results from the motion detector. This option, depicted in block 760, could decrease perceived sync-up time (by users) between controllers and consoles. In fact, such communications could actually be initiated before any user even touches a controller device (or as a user is approaching a controller device), as is shown at block 770.

Figure 8:
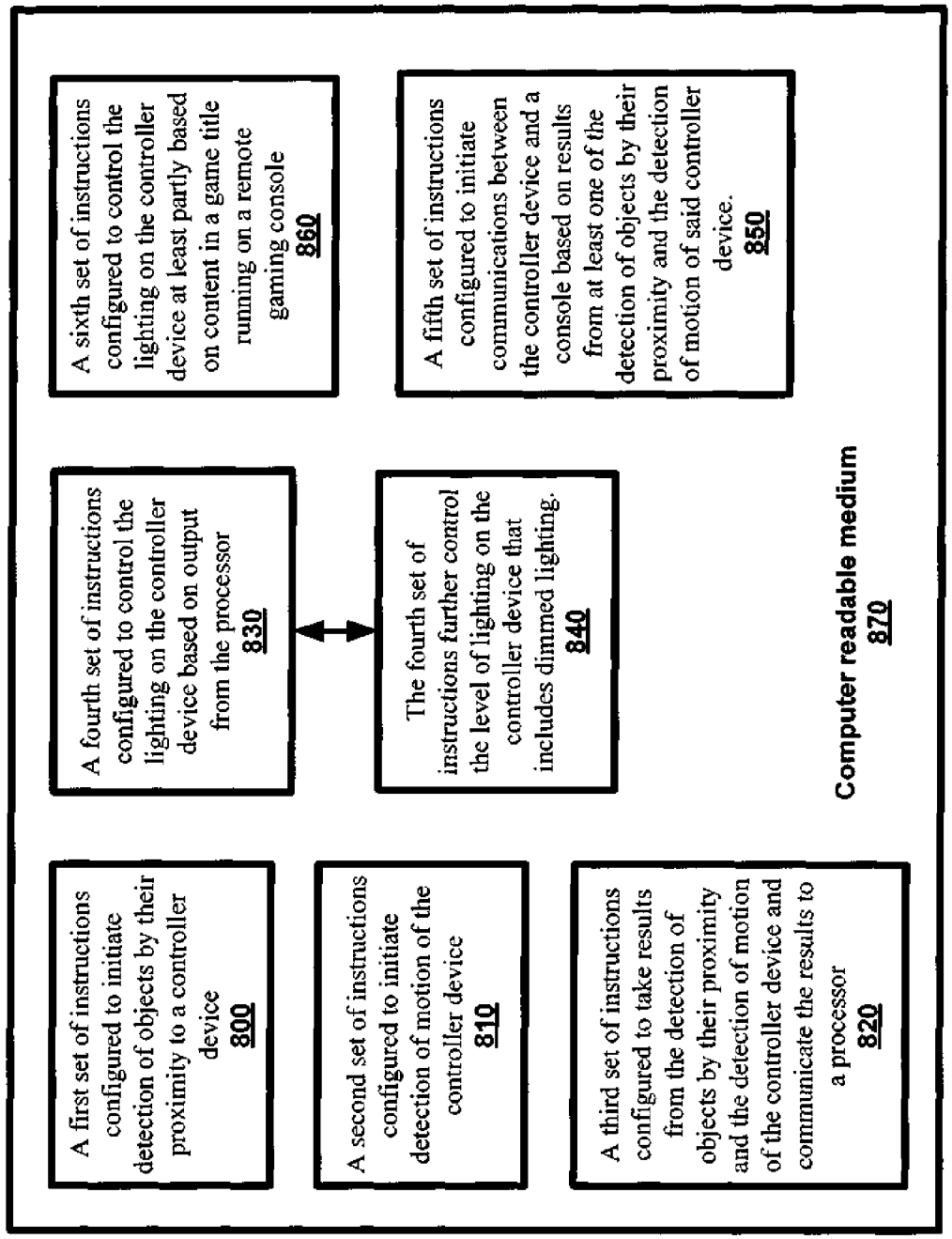
FIG. 8 illustrates an exemplary computer readable medium for implementing the presently disclosed subject matter.

FIG. 8 illustrates an exemplary computer readable medium for controlling at least part of the lighting on controller devices configured to communicate with computing. As was indicated above with the other mechanisms, it should be understood that this subject matter could be implemented in systems, methods, and other mechanisms. Turning to FIG. 8, at block 800, a first set of instructions can be configured to initiate detection of objects by their proximity to a controller device. At block 810, a second set of instructions can be configured to initiate detection of motion of the controller device. At block 820, a third set of instructions can be configured to take results from the detection of objects by their proximity and the detection of motion of the controller device and communicate the results to a processor. Finally, at block 830, a fourth set of instructions can be configured to control the lighting on the controller device based on output from the processor. These instructions can be supported with other instructions, as those of skill in the art will appreciate, to implement the above discussed subject matter.

For example, the fourth set of instructions can further control the level of lighting on the controller device that includes dimmed lighting (as shown at block 840). Alternatively, a fifth set of instructions can initiate communications between the controller device and a console based on results from at least one of the detection of objects by their proximity and the detection of motion of said controller device, in order to give the appearance that such communications are established instantaneously (as shown at block 850. Additionally, a sixth set of instructions can be configured to control the lighting on the controller device at least partly based on content in a game title running on a remote gaming console (as shown at block 860). Other instructions can also be included based on the above provided disclosure.

Figure 9:
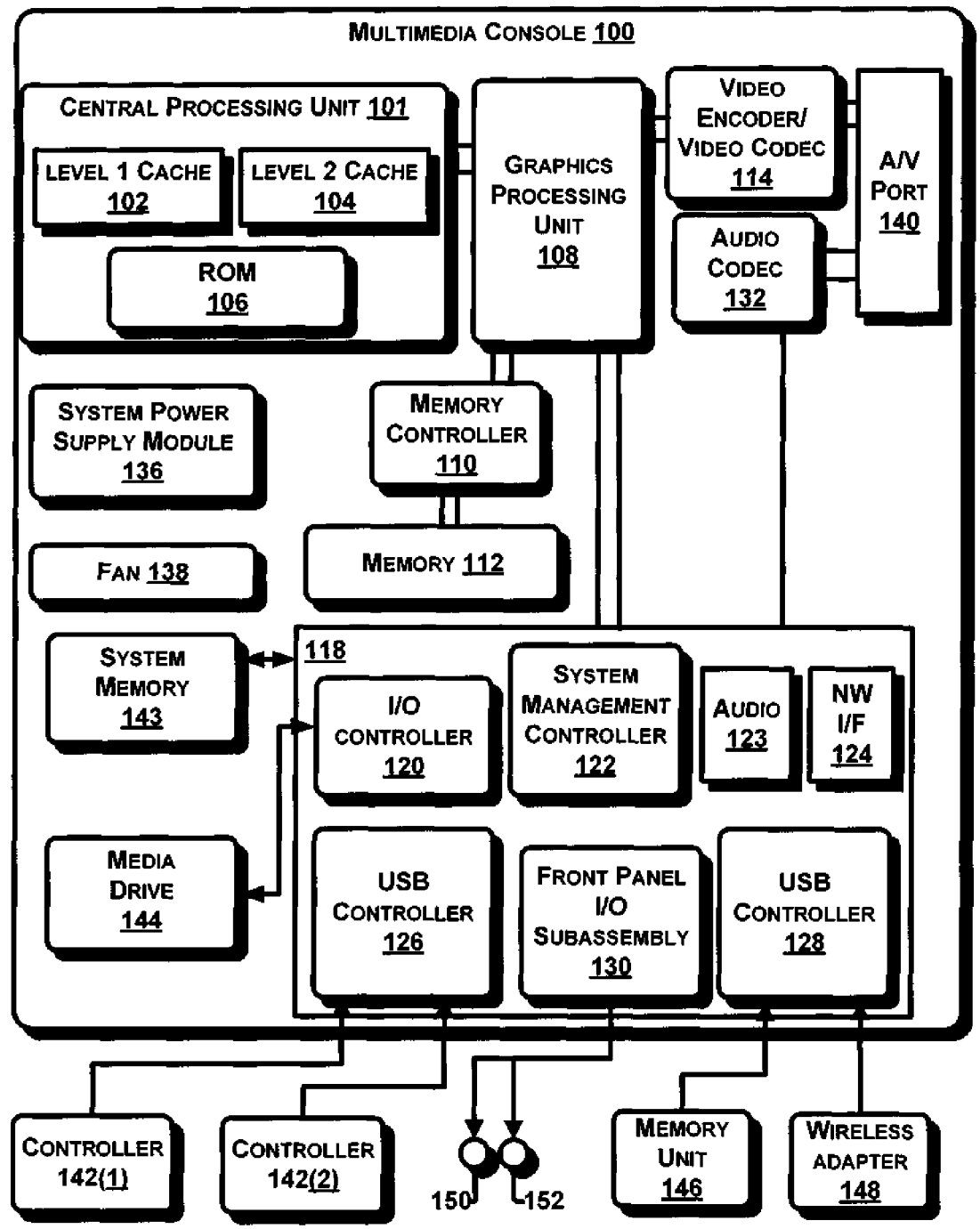
FIG. 9 illustrates an exemplary computing device, such as a console, that can be used in conjunction with the various aspects of the present disclosure discussed with reference to FIGS. 1-8 and 10.

Exemplary Computing Devices and Networks for Lighting Activation by Proximity and Motion The above discussed computing devices and accessories can be embodied as gaming consoles, music players, personal computers, controllers, remote control devices and other such devices having different, similar, or the same platforms. Referring to FIG. 9, a block diagram shows an exemplary multimedia console that can be used in conjunction with the various accessories with lighting activation by proximity and motion capabilities.

This console, which includes a game oriented console or a PC, can comprise, for example, digital audio processing functionality. Specifically, in FIG. 9, a multimedia console 100 is shown, with a central processing unit (CPU) 101 having a level 1 (L1) cache 102, a level 2 (L2) cache 104, and a flash ROM (Read-only Memory) 106. The level 1 cache 102 and level 2 cache 104 can temporarily store data and hence reduce the number of memory access cycles, thereby improving processing speed and throughput. The flash ROM 106 can store executable code that is loaded during an initial phase of a boot process when the multimedia console 100 is powered. Alternatively, the executable code that is loaded during the initial boot phase can be stored in a flash memory device (not shown). Further, ROM 106 can be located separately from the CPU 101. These memory devices can cache parts or the entirety of the above mentioned applications, programs, applets, managed code, and so on. Moreover, these memory devices can store sensitive and non-sensitive information on a memory unit-by-memory unit basis, as was discussed above. Any of such information can be used at least in part to aid in activating lighting by proximity and motion.

A graphics processing unit (GPU) 108 and a video encoder/video codec (coder/decoder) 114 can form a video processing pipeline for high speed and high resolution graphics processing. Data can be carried from the graphics processing unit 108 to the video encoder/video codec 114 via a bus. The video processing pipeline can output data to an A/V (audio/video) port 140 for transmission to a television or other display. A memory controller 110 can be connected to the GPU 108 and CPU 101 to facilitate processor access to various types of memory 112, such as, but not limited to, a RAM (Random Access Memory). Thus, various types of information, whether sensitive or not, or even parts of various types of information, can be stored in the various types of memories discussed above, depending on the need.

The multimedia console 100 can include an I/O controller 120, a system management controller 122, an audio processing unit 123, a network interface controller 124, a first USB host controller 126, a second USB controller 128 and a front panel I/O subassembly 130 that can be preferably implemented on a module 118. The USB controllers 126 and 128 can serve as hosts for peripheral controllers 142(1)-142(2), a wireless adapter 148, and an external memory unit 146 (e.g., flash memory, external CD/DVD ROM drive, removable media, etc.). Such peripheral controllers 142(1)-142(2) can have various types of lighting displays that is triggered by proximity and motion. Moreover, the network interface 124 and/or wireless adapter 148 can provide access to a network (e.g., the Internet, home network, etc.) and can be any of a wide variety of various wired or wireless interface components including an Ethernet card, a modem, a Bluetooth module, a cable modem, and the like.

System memory 143 can be provided to store application data that is loaded during the boot process. A media drive 144 can be provided and can comprise a DVD/CD drive, hard drive, or other removable media drive, etc. The media drive 144 can be internal or external to the multimedia console 100. Application data can be accessed via the media drive 144 for execution, playback, etc. by the multimedia console 100. The media drive 144 can be connected to the I/O controller 120 via a bus, such as a Serial ATA bus or other high speed connection (e.g., IEEE 1394). Additional to such application data, other information can be stored on the console 100 that will aid in the communication between peripheral/accessory device controllers and the console 100 itself.

The system management controller 122 can provide a variety of service functions to assure the availability of the multimedia console 100. The audio processing unit 123 and an audio codec 132 can form a corresponding audio processing pipeline with high fidelity, 3D, surround, and stereo audio processing according to aspects of the presently disclosed subject matter above. Audio data can be carried between the audio processing unit 123 and the audio codec 126 via a communication link. The audio processing pipeline can output data to the A/V port 140 for reproduction by an external audio player or device having audio capabilities.

The front panel I/O subassembly 130 can support the functionality of the power button 150 and the eject button 152, as well as any LEDs (light emitting diodes) or other indicators exposed on the outer surface of the multimedia console 100. Thus, the proximity and motion lighting discussed herein is not limited to the peripheral/accessory devices, but also extends to the console 100 itself and to other computing devices. A system power supply module 136 can provide power to the components of the multimedia console 100. A fan 138 can cool the circuitry within the multimedia console 100.

The CPU 101, GPU 108, memory controller 110, and various other components within the multimedia console 100 can be interconnected via one or more buses, including serial and parallel buses, a memory bus, a peripheral bus, and a processor or local bus using any of a variety of bus architectures.

When the multimedia console 100 is powered on or rebooted, application data can be loaded from the system memory 143 into memory 112 and/or caches 102, 104 and executed on the CPU 101. Such application data can include some of the online derived data. The application can also present a graphical user interface that provides a consistent user experience when navigating to different media types available on the multimedia console 100. In operation, applications and/or other media contained within the media drive 144 can be launched or played from the media drive 144 to provide additional functionalities to the multimedia console 100.

The multimedia console 100 can be operated as a standalone system by simply connecting the system to a television or other display. In this standalone mode, the multimedia console 100 can allow one or more users to interact with the system, watch movies, listen to music, and the like. However, with the integration of broadband connectivity made available through the network interface 124 or the wireless adapter 148, the multimedia console 100 can further be operated as a participant in a larger network community of computing devices. As such a participant, it can interact with computing devices, whether PCs or servers, and receive information that can be eventually stored.

Figure 10:
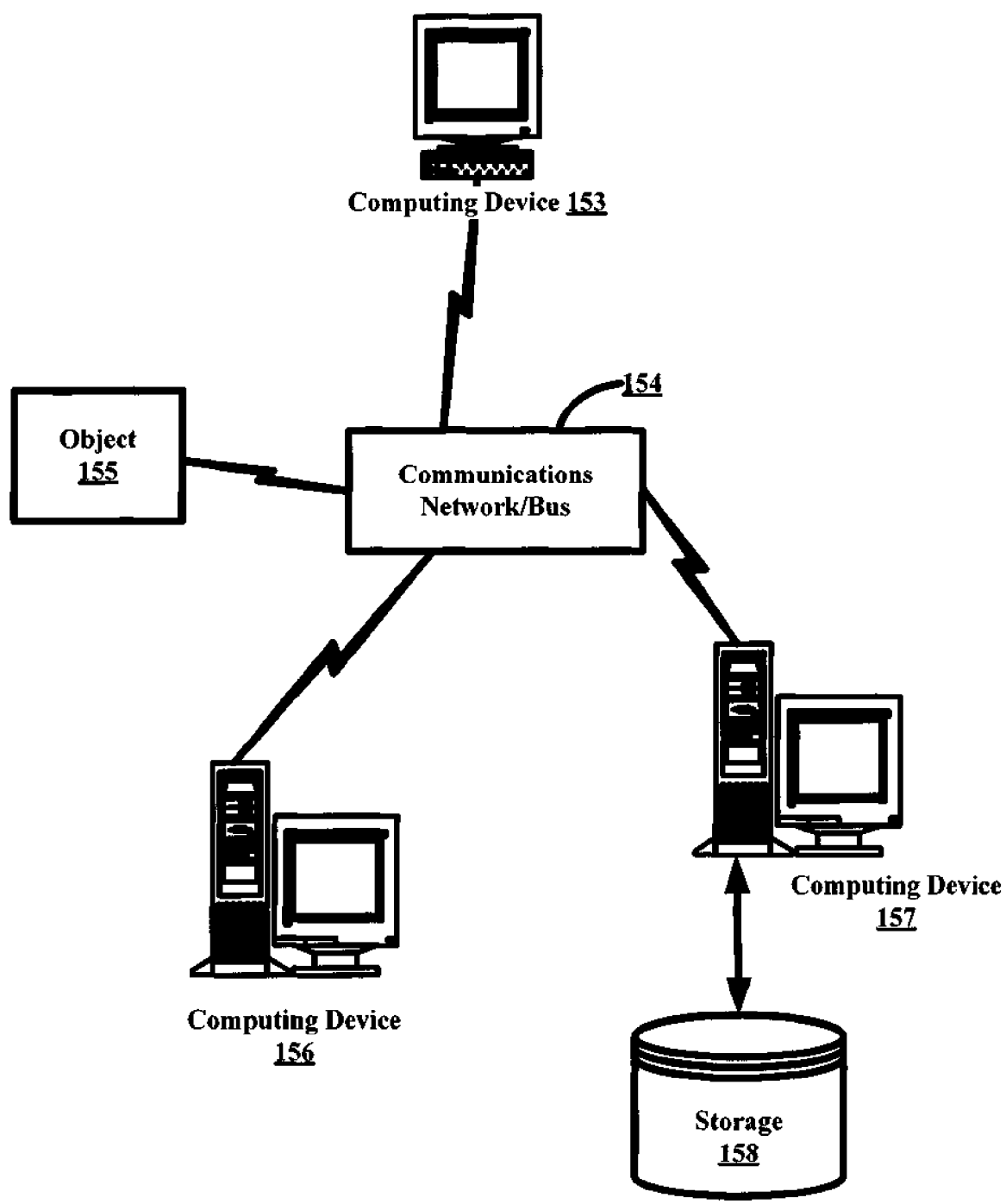
FIG. 10 illustrates an exemplary networking environment for the presently disclosed subject matter discussed with reference to FIGS. 1-9.

Next, FIG. 10 illustrates an exemplary networking environment for subject matter discussed with reference to FIGS. 1-9. The above discussed console 100 can correspond to any one of the aforementioned computing devices, or it can be distributed over such devices. It can interact with various other objects 155 and storage devices 158 via a communications network/bus 154, where such objects 155 and devices 158 can correspond to other computing devices (whether hardware, firmware, or software). The controllers 142(1)-142(2) can communicate with the console 100 in a wired manner or wirelessly, over close distances or over remote distances using the shown communications network 154. Such communication can be aided by various computing devices 156, 153, 157 connected to the communications network 154.

Finally, it should also be noted that the various techniques described herein can be implemented in connection with hardware or software or, where appropriate, with a combination of both. Thus, the methods and apparatus of the presently disclosed subject matter, or certain aspects or portions thereof, can take the form of program code (i.e., instructions) embodied in tangible storage media, such as floppy diskettes, CD-ROMs, hard drives, or any other machine-readable storage medium, where, when the program code is loaded into and executed by a machine, such as a computer, the machine becomes an apparatus for practicing the subject matter.

In the case of program code execution on programmable computers, the computing device can generally include a processor, a storage medium readable by the processor (including volatile and non-volatile memory and/or storage elements), at least one input device, and at least one output device. One or more programs that can utilize the creation and/or implementation of domain-specific programming models aspects of the present invention, e.g., through the use of a data processing application programming interface (API) or the like, are preferably implemented in a high level procedural or object oriented programming language to communicate with a computer system. However, the program(s) can be implemented in assembly or machine language, if desired. In any case, the language can be a compiled or interpreted language, and combined.

Finally, while the present disclosure has been described in connection with a plurality of exemplary aspects, as illustrated in the various figures and discussed above, it is understood that other similar aspects can be used or modifications and additions can be made to the described aspects for performing the same function of the present disclosure without deviating therefrom. For example, in various aspects of the disclosure, methods, systems, and computer readable media were described configured for providing lighting to electronic devices by taking proximity and motion into account. However, other equivalent mechanisms to these described aspects are also contemplated by the teachings herein. Therefore, the present disclosure should not be limited to any single aspect, but rather construed in breadth and scope in accordance with the appended claims.

What is claimed:

1. A system for controlling lighting activation on controller devices configured to communicate with gaming consoles, comprising:
    a proximity detector configured to detect the presence of individuals substantially around or touching a controller device, the proximity of an individual to said controller device is detected based on a predetermined standard;
    a motion detector configured to detect the motion of said controller device, the motion is determined from the output from at least one of an accelerometer device or a gyroscope device;
    a manager component configured to receive input data from said proximity detector and input data from said motion detector;
    said manager component is configured to determine whether said individual is moving through a range of distances from the controller device based on changes in said input data from said proximity detector, the range of distance comprising at least a first distance, a second distance, and touching the controller device, and said manager component configured to determine the distance in the range of distances where the individual is;
    said manager component is configured to determine whether and how said controller device is being moved by said individual based on said input data from said motion detector;
    said manager component is configured to control the lighting level of at least one light of a plurality of lights on said controller device based on said input data from said proximity detector and said motion detector; and
    said manager component is configured to control said at least one light of said plurality of lights based on movement of at least one object in a game.

2. The system according to claim 1, wherein said lighting level can be set to at least one of a maximum setting, an off setting, and a range of dimmed settings in between said maximum setting and said off setting.

3. The system according to claim 1, wherein whether said individual is holding said controller device is based on a first capacitance level and whether said individual is moving though a range of distances to said controller device is based on a changing capacitance level.

4. The system according to claim 1, wherein whether said controller device is being moved by said individual is based on an acceleration data or gyroscope data level and how said controller device is being moved by said individual is based on a changing acceleration data or gyroscope data.

5. The system according to claim 1, wherein lighting intensity of said at least one light of said plurality of lights is controlled via pulse width modulation.

6. The system according to claim 1, wherein said manager component is configured to control said at least one light of said plurality of lights by controlling color, intensity, and pattern of said at least one light over a period of time depending on said input data from said proximity detector and said motion detector.

7. The system according to claim 1, wherein said manager component is configured to control said at least one light of said plurality of lights based on motion of said individual.

8. The system according to claim 1, wherein said system resides in one of said controller device, a gaming console, and at least partly in said controller device and at least partly in said gaming console.

9. The system according to claim 1, wherein said manager component starts radio frequency communications between a gaming console and said controller device based on data from said proximity detector.

10. The system according to claim 9, wherein said predetermined standard is at least one of capacitance, light, including visible light or infrared light, and ultrasonic sound.

11. The system according to claim 1, wherein said controller device is at least one of (a) a traditional gaming controller, (b) a joystick, (c) a steering wheel, (d) a microphone, (e) a music device, and (f) a gesture input device.

12. A method for controlling lighting activation on a controller device configured to communicate with a remote gaming console, comprising:
    detecting with a proximity detector a predetermined unit of measurement about said controller device;
    forwarding results from said proximity detector to a manager component;
    detecting with a motion detector movement of said controller device;
    forwarding results from said motion detector to said manager component;
    receiving from the remote gaming console, information indicative of movement of at least one object in a game;
    processing said results from said proximity detector, said information indicative of movement of at least one object in said game from the remote gaming console, and said results from said motion detector in order to set a light from a plurality of lights on said controller device; and
    setting said light to a first level based on determining, from said input data from said proximity detector, whether an individual is at a first distance in a range of distances to said controller device, the range of distances comprising the first distance, a second distance, and holding said controller device.

13. The method according to claim 12, wherein said first level is at least one of (a) a maximum light level, (b) a minimum light level, and (c) a intermediate light level between said maximum light level and said minimum light level.

14. The method according to claim 12, further comprising initiating communications between said controller device and a gaming console after processing at least one of said results from said proximity detector and said results from said motion detector.

15. The method according to claim 14, wherein said communications are configured to initiate before a user touches said controller device.

16. A computer readable tangible storage medium storing thereon computer executable instructions for controlling at least part of the lighting on controller devices configured to communicate with computing devices, comprising:
    a first set of instructions configured to initiate detection of objects by their proximity to a controller device;
    a second set of instructions configured to initiate detection of motion of said controller device;
    a third set of instructions configured to take results from said detection of objects by their proximity and said detection of motion of said controller device;
    a fourth set of instructions configured to control the lighting on said controller device based on determining from the results from said third set of instructions whether an object is moving through a range of distances to said controller device based on detection from said first set of instructions, the range of distances comprising a first distance, a second distance, and touching the controller device;
    a fifth set of instructions configured to control the lighting on said controller device based on output from said controller indicative of whether a user is holding said controller device based on detection from said first set of instructions; and
    a sixth set of instructions configured to control the lighting on said controller device based on output from a gaming console, the output indicative of movement of at least one object in a game.

17. The computer readable medium according to claim 16, wherein said fourth set of instructions further controls the level of lighting on said controller device that includes dimmed lighting.

18. The computer readable medium according to claim 16, further comprising a fifth set of instructions that initiates communications between said controller device and a console based on results from at least one of said detection of objects by their proximity and said detection of motion of said controller device.

19. The computer readable medium according to claim 16, further comprising a sixth set of instructions that controls said lighting on said controller device at least partly based on content in a game title running on a remote gaming console.

* * * * *